United States Patent [19]

Foley

[11] 4,028,391
[45] June 7, 1977

[54] METHOD OF PREPARING ORGANOSILICON CARBOXYLATES

[75] Inventor: Kevin M. Foley, Hebron, Ohio

[73] Assignee: Owens-Corning Fiberglas Corporation, Toledo, Ohio

[22] Filed: Jan. 6, 1975

[21] Appl. No.: 538,661

Related U.S. Application Data

[63] Continuation-in-part of Ser. No. 428,279, Dec. 26, 1973, abandoned.

[52] U.S. Cl. .................. 260/448.2 D; 260/448.2 E
[51] Int. Cl.$^2$ .......................................... C07F 7/08
[58] Field of Search ............. 260/448.2 E, 448.2 D

[56] References Cited

UNITED STATES PATENTS

| 2,537,073 | 8/1951 | MacKenzie | 260/448.2 E X |
| 2,566,347 | 9/1951 | MacKenzie | 260/448.2 E X |
| 3,542,831 | 11/1970 | Gowdy | 260/448.2 E |
| 3,542,832 | 11/1970 | Roth | 260/448.2 E |

Primary Examiner—Paul F. Shaver
Attorney, Agent, or Firm—John W. Overman; William P. Hickey; Philip R. Cloutier

[57] ABSTRACT

Halogen and amine groups attached to silicon are replaced by organocarboxylate groups. The replacement is carried out with the reactants dissolved in pentane. Substantially quantitative yields are obtained, and the reaction can be preceded or followed by other reactions carried out in the pentane media. For example, trichlorosilane is reacted with an olefinic unsaturate containing halogen in a first stage reaction. Thereafter the product of the reaction is reacted with an organic acid so that the chlorines attached to the silicon are then replaced by the organocarboxylate groups in a second stage reaction. The remaining halogen is then replaced by amine in a third stage reaction, all in the pentane media. All this is accomplished without an HCl scavenger.

1 Claim, No Drawings

METHOD OF PREPARING ORGANOSILICON CARBOXYLATES

The present application is a continuation-in-part application of my co-pending application Ser. No. 428,279, filed Dec. 26, 1973, now abandoned.

BACKGROUND OF THE INVENTION

The prior art processes with which I am aware for replacing halogen or amine groups attached to silicon by organocarboxylate groups involve a reaction between a carboxylic acid and a halosilane and use amines to scavenge the HCl liberated. By way of example, trichlorosilane and acetic acid diluted in benzene give a yield of approximately 40 percent of theoretical. The same is true using toluene and other prior art solvents with which I am aware. As part of these processes, therefore, it is necessary to distill or otherwise remove the reactants, scavenging agents, and other impurities that are formed from the desired product. In the prior art processes, an appreciable amount of siloxane is produced during the reaction and during the distillation.

The precursor for many of the organosilicon carboxylates presently produced are halogenated silanes and usually chlorinated silanes. Organo groups can be coupled to the silicon atoms by the reaction of silane hydrogen with an olefinic double bond. The product is usually purified by distillation and thereafter the halogens that are attached to the silicon are replaced by organocarboxylate groups such as alkylcarboxyl or arylcarboxyl groups in a second stage reaction. Because of the poor yield that is obtained during the alkylcarboxyl or arylcarboxyl formation, another distillation step is required before substitutions can be made on organo groups attached to the silicon atoms. Because the organocarboxyl substitutions of the prior art give numerous impurities and because of the elevated temperature used in the distillation step, a considerable amount of siloxane is formed and this further decreases the yield. By the time that the prior art has carried out all of the reaction and distillations above referred to, the yield of the product produced is at best a very small percentage of theoretical.

The principal object of the present invention is the provision of a new and improved process for replacing halogens or amine groups attached to a silicon atom by carboxyl groups without using scavenging agents, and in a manner giving better yields than have been possible with prior art processes.

Further objects and advantages will become apparent to those skilled in the art from the following description of the preferred embodiments.

DESCRIPTION OF THE PREFERRED EMBODIMENTS

The prior art has carried out the reaction between a halogenated silane and an organic acid as a solution of various organic solvents including benzene, toluene, ethers, etc. In one instance with which I am aware (U.S. Patent 2,537,073) the reaction is carried out in a small amount of pentane but the amount of pentane used is too little to achieve the advantages of the present invention. In all reported processes with which I am aware wherein a trihalosilane is reacted with an organic acid without using a scavenging agent, the yield of tricarboxylatosilane produced has been less than quantitative and in most cases below approximately 50% of theoretical. In the reaction of trichlorosilane and acetic acid, the prior art has found it necessary to keep the reaction time short, i.e. approximately 1 minute, but even using these precautions the yields obtained were not more than approximately 50%.

According to the present invention it has been discovered that when the reaction is carried out using sufficient pentane to adequately separate the silane molecules that almost theoretical yields can be obtained. Normally pentane is not as good a solvent as is benzene, toluene or the ethers, nevertheless, improved results are had. It appears that when a trihalosilane such as trichlorosilane or tribromosilane is used as starting material, the trialkylcarboxylatosilane and triarylcarboxylatosilane is formed without producing tetraalkylcarboxylatosilane or tetraarylcarboxylatosilane as occurs in prior art processes. Also it has been found that the hydrogen chloride scavengers used in prior art processes are not necessary when the reaction is carried out in pentane. It further appears that the pentane media can be used as a media for reacting silane hydrogen with an olefin. This is usually carried out before reacting the silane with the acid or anhydride, and when this is performed in a pentane media no purification or distillation is necessary between the two reactions. It has further been found that subsequent reactions can also be carried out in pentane, so that the trialkylcarboxylatosilane or triarylcarboxylatosilane product can be left in the pentane for these reactions. In fact the product need never be distilled, since the pentane solution is compatible with most materials that are normally used as a coating for glass fibers.

EXAMPLE 1

A 0.5707 g. mole portion of trichlorosilane is placed in a 1,000 ml. flask together with 450 ml. of pentane. A reflux condenser is installed on the flask together with an addition funnel and 1.712 g. moles of acetic acid in 100 ml. of pentane is added to the addition funnel. The acetic acid solution is slowly added to the flask over a period of 34 minutes. The contents of the flask are heated to reflux for one hour. 126.7 g. of

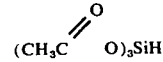

(0.487 moles) is isolated. This is a yield of 85.3%.

EXAMPLE 2

The process of Example 1 is repeated excepting that

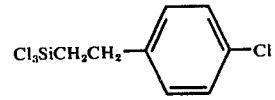

is substituted for the trichlorosilane and the product

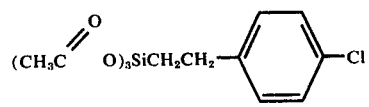

was obtained in 90.4% yield.

EXAMPLE 3

The process of Example 1 is repeated excepting that formic acid is substituted for acetic acid and

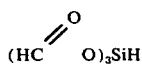

is obtained in an 86% yield.

EXAMPLE 4

The process of Example 1 is repeated excepting that butyric acid is substituted for acetic acid and the product

is obtained in an 89% yield.

EXAMPLE 5

The process of Example 1 is repeated excepting that benzoic acid is used in place of acetic acid and the reaction product

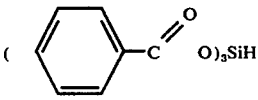

is obtained in an 86% yield.

EXAMPLE 6.

0.5 gram mole of trichlorosilane is placed in a 1,000 ml. flask with 450 ml. of pentane. The flask is equipped with a reflux condenser. 0.5 ml. of a chloroplatinic acid solution (10 g chloroplatinic acid in 150 ml. isopropanol) is added. Acetylene gas is bubbled through the pentane solution. An approximately 100% yield of $Cl_3SiCH=CH_2$ is produced. The system is purged with nitrogen, 3 g of aluminum chloride are added, and 0.5 moles of chlorobenzene dissolved in 100 ml. of pentane is then added to the flask under reflux conditions. A substantially 100% yield of

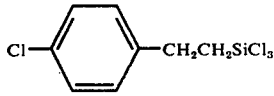

is produced. Thereafter, 1.5 moles of acetic acid dissolved in 100 ml. of pentane is added to the flask using reflux over a period of 15 minutes, and the product

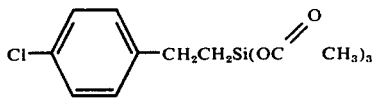

is produced with an 84% yield based on the original amount of trichlorosilane used.

EXAMPLE 7

A 0.5 mole sample of trichlorosilane is placed in a 1,000 ml. flask together with 450 ml. pentane. The flask is equipped with a reflux condenser. 0.5 ml. of a chloroplatinic acid solution (10 g chloroplatinic acid in 150 ml. of isopropanol) is added to the flask. 0.5 mole of styrene is added to the flask under refluxing conditions over a period of 40 minutes. An 80% yield of

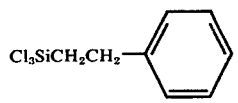

is obtained.

EXAMPLE 8

The process of Example 7 is repeated excepting that subsequent to the reaction of the styrene, 1.5 moles of acetic acid in 100 ml. of pentane are added to the flask over a period of 40 minutes using reflux to produce the product

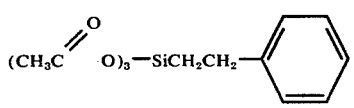

in an approximate 85% yield.

EXAMPLE 9

The process of Example 8 is repeated excepting that pentene-2 is used in place of styrene. The product

is obtained in an approximately 95% yield.

EXAMPLE 10

The process of Example 1 is repeated excepting that the trichlorosilane is replaced by aminotrimethylsilane, and only 1.16 moles of acetic acid is used. The product

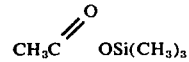

is obtained in an approximately 85% yield.

EXAMPLE 11

0.667 mole of 1-tridecene is placed in a one liter flask equipped with a reflux condenser and 0.5 g of benzoyl peroxide catalyst is added thereto. Thereafter 0.7616 mole of trichlorosilane is slowly added with reflux keeping the contents of the flask above 130° C. The heating is continued for approximately 2½ hours at which time the pot temperature reaches 200° C. The pot is thereafter allowed to cool to room temperature. 300 ml. of pentane is then added to the pot and 2.668 mole of heptanoic acid dissolved in 200 milliliters of pentane are added slowly with stirring. The pot is heated to refluxing conditions during the addition, and the heating is continued for 1 hour and 50 minutes. 91.3% of

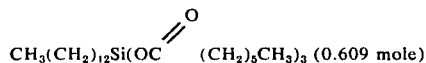

is obtained.

EXAMPLE 12

4 moles of benzene, 8 moles of vinyltrichlorosilane, and 20 grams of aluminum chloride are reacted together under refluxing conditions for 16 hours. 2500 ml. of pentane are then added, followed by 27.2 moles of formic acid. Obtained from this reaction are 0.523 mole (13.1%) of

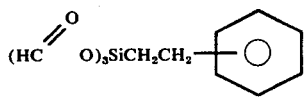

and 1.74 moles (43.5%) of

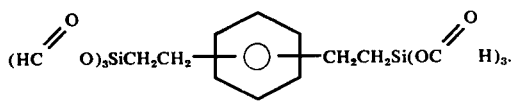

EXAMPLE 13

The process of Example 11 is repeated excepting that the product is not separated from the pentane. A size for glass fibers is made of the following materials:

| | |
|---|---|
| Reaction solution of Example 11 | 60 grams |
| Isopropanol | 60 grams |
| Polyethylene emulsion--20% solids (Quaker Quasoft HS60) | 480 grams |
| Deionized water | 3400 grams |

The size is prepared by dissolving the pentane solution of the reaction product in the isopropanol. The polyethylene emulsion is added to a mix tank containing an agitator and the isopropanol-pentane solution of the silane is slowly added to the mix tank with agitation. The silane is slowly taken up by the emulsified particles of polyethylene without disrupting the emulsion in any way. Thereafter the deionized water is added and the thinned emulsion is added to glass fibers at forming. The sized fibers produced have a good lubricious feel and have low running tensions when pulled over guide eyes.

EXAMPLE 14

A size for glass fibers is produced according to Example 13 excepting that the reaction solution of Example 12 is substituted for the reaction solution of Example 11. This material is applied to a sliver of glass fibers 0.00035 inch in diameter grouped to give 1500 yds. per 1 pound and the coated fibers are coiled into a package which is then dried at 265° F for 16 hours. These fibers are then coated with an impregnate material having the following composition according to U.S. Pat. No. 3,567,671:

| Material | Parts By Weight |
|---|---|
| Water | 930 |
| Sodium hydroxide | 1 |
| Resorcinol formaldehyde latex (75% solids) | 48 |
| Ammonium hydroxide (26° Be.) | 8 |
| Formaldehyde (37% solids) | 16 |
| Vinyl-pyridine, styrene, butadiene terpolymer latex (41% solids) | 900 |
| Vinyl chloride, vinylidene chloride copolymer latex (50% solids) | 350 |
| Paraffin wax emulsion (55% solids) | 200 |

The coated fibers are dried in an oven heated to 510° F for 1 minute. Three coated slivers are twisted together into strands and 6 inch lengths of this strand are laid side by side in touching engagement between two layers of 20 mil thick styrenebutadiene rubber sheet stock. The sandwich is placed in a mold heated to 350° F and pressed at 100 psi for 20 minutes. The sandwich is 1 inch wide and it requires a force of 60 pounds to pull the rubber layers from the impregnated strands.

Any type of aminosilane or halogen silane can be used in the process. For example: iodosilane, bromosilane, and chlorosilane, and particularly the trihalogen silanes can be used as a starting material.

Any material having a COOH group attached thereto can be used as a source of hydrogen to replace the halogen or amine group attached to the silicon atom. Preferred materials are the acids having no more than 20 carbon atoms. These materials may contain functional groups, as for example, ether, oxygen, amine groups, halogen groups, olefinic double bonds, aryl groups, OH groups, etc. The higher molecular weight acids can be used inasmuch as their solubility in pentane increases with molecular weight.

Substantially any organo acid having an olefinic double bond or acetylenic triple bond can be reacted with silane hydrogen in the present of pentane. These organic acids having olefinic double bonds or acetylenic triple bonds can have other than hydrocarbon groups as a part thereof. These groups can include hydroxyl groups, aryl groups, amine groups, halogen groups, etc. Even though these groups are reactive, the reaction of silane hydrogen with the double or triple bond proceeds at such a low temperature in pentane that it proceeds in preference to a reaction of substantially any other functional group including an oxirane group. What is more, the alkylcarboxyl or arylcarboxyl production by the displacement of halogen attached to silicon proceeds in pentane so easily and completely that this step can be carried out even though other functionality exists on the reactant containing the COOH group. Substantially any free radical catalyst can be used for the reaction of silane hydrogen with an olefinic double bond. Where the reactant has a double bond in various positions and a substitution in the alpha position only is desired, chloroplatinic acid is the preferred catalyst.

As pointed out above, the organosilane product, for example, alkylcarboxylate or arylcarboxylate product, can be left dissolved in the pentane solution to undergo a further reaction of the organo portion attached to the silicon atom. Many of these products, and particularly the higher molecular weight organo products are soluble in the pentane, while water and HCl are not appreciably soluble in the pentane, so that a reaction product kept in the pentane media has prolonged shelf life. What is more, the organosilane products dissolved in the pentane can be used as a glass coupling agent without separation from the pentane since a dilute solution of the organosilane will usually be desired to aid in the wetting out of the surface of the glass. In addition, pentane has a sufficiently low chain length that it is soluble in the lower molecular weight prepolymer materials that are used in the sizing ingredients for glass fibers. The pentane solution of the reaction products of the method of the present invention, therefore, can be used as a size ingredient for application to glass fibers without further treatment, distillation, etc.

In order for the high yields and other advantages of the present invention to be had, the silane molecules must be separated by sufficient pentane so that the siloxanes do not form to any appreciable extent. It has been found that critical amounts of pentane exist and that more than approximately 600 milliliters per gram mole of the silane must be used in order that an improvement in the yields will be obtained. Preferably the amount of pentane to be used should be more than 650 milliliters per gram mole of the silane. This is shown by the following Examples:

EXAMPLE 15

The process of Example 1 is repeated using 0.5707 gram mole of ethyltrichlorosilane and 338 milliliters of pentane instead of the 450 milliliters of pentane as the initial charge to the flask. The acetic acid was similarly diluted in an additional 100 milliliters of pentane. 119.3 grams of

was produced. This is a yield of 89.2%.

EXAMPLE 16

The process of Example 15 is repeated excepting that the initial charge to the flask contained only 225 milliliters of pentane. In this case only 81.8 grams of

was obtained. This is a yield of 61.2%.

Other experiments which have been run with organo silanes of higher molecular weight and/or acids of higher molecular weight show that the molecular weights of reactants do not appreciably affect the critical limit of the amount of pentane that is necessary to give the improved yields of the present invention.

It will be seen that the present invention has utility in several types of reaction wherein it improves yields and permits successive reactions without purification of the products after each reaction. The invention has particular advantage in replacing halogen and amine groups from silicon atoms of an organo silicon material with an organocarboxylate group. The organosilicon material can be any monomer or polymer soluble in pentane. The silicon atoms thereof can be the sole silicon atom of the compound or can be one of a number of silicon atoms connected by organo groups or oxygen atoms. Preferred organocarboxylate groups are those obtained by the removal of hydrogen from an organic acid. Therefore one aspect of the invention is indicated by the production of the following radical:

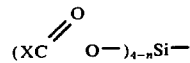

wherein: $n$ is 1 to 3 and

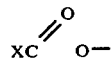

is an organocarboxylate group preferably obtained from an acid reacting with the radical:

wherein: $Y$ is a halogen or amine group.

One large class of products made by the reaction of the invention is:

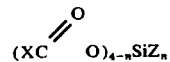

wherein: $Z$ is an organo group preferably having functionality for coupling to organic resins. This functionality will include olefinic double bonds, oxirane groups, amine groups, carboxyl groups and alcohol groups.

While the invention has been described in considerable detail, I do not wish to be limited to the particular embodiments described, and it is my intention to cover hereby all novel adaptations, modifications, and arrangements thereof which come within the practice of those skilled in the art to which the invention relates.

I claim:

1. A coupling agent for glass fibers comprising from 95 to 50 weight percent pentane and from 5 to 50 weight percent of an organosilane having the formula

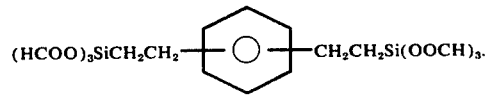

* * * * *